United States Patent [19]

Hanson

[11] Patent Number: 4,559,051
[45] Date of Patent: Dec. 17, 1985

[54] DISPOSABLE INCONTINENCE DIAPER

[76] Inventor: James P. Hanson, 8516 W. G Ave., Kalamazoo, Mich. 49009

[21] Appl. No.: 515,012

[22] Filed: Jul. 18, 1983

[51] Int. Cl.⁴ .................. A61F 13/16; A61F 13/18
[52] U.S. Cl. .................... 604/385 R; 604/378
[58] Field of Search .......... 604/347, 349, 351, 353, 604/354, 358, 367, 378, 379, 385–387, 389, 397

[56] References Cited

U.S. PATENT DOCUMENTS

| | | | |
|---|---|---|---|
| Re. 20,315 | 3/1937 | Lesueur | 128/284 |
| Re. 28,483 | 7/1975 | Ralph | 128/289 |
| 584,204 | 6/1897 | Bowles . | |
| 1,217,014 | 2/1917 | Knieriem . | |
| 1,224,756 | 5/1917 | Laing . | |
| 1,833,960 | 12/1931 | Alsop . | |
| 1,971,671 | 8/1934 | Alsop | 128/284 |
| 1,977,604 | 11/1934 | Alsop | 128/284 |
| 2,004,088 | 6/1935 | Alsop | 128/284 |
| 2,201,255 | 5/1940 | Wilson, Jr. | 128/284 |
| 2,273,906 | 2/1942 | Spanel | 128/284 |
| 2,445,220 | 7/1948 | Issacson | 128/295 |
| 2,532,029 | 11/1950 | Medoff | 128/287 |
| 2,556,800 | 6/1951 | Donovan | 128/287 |
| 2,575,163 | 11/1951 | Donovan | 128/287 |
| 2,575,164 | 11/1951 | Donovan | 128/287 |
| 2,575,165 | 11/1951 | Donovan | 128/287 |
| 2,664,895 | 1/1954 | Shulman | 128/287 |
| 2,691,983 | 10/1954 | Bernard | 128/284 |
| 2,754,824 | 7/1956 | Blaufus | 128/284 |
| 2,817,338 | 12/1957 | Slusser | 128/286 |
| 2,854,979 | 10/1958 | Turner et al. | 128/287 |
| 2,873,740 | 2/1959 | Wainwright | 128/295 |
| 2,895,477 | 7/1959 | Bernard | 128/284 |
| 2,956,564 | 10/1960 | Ohara | 128/287 |
| 3,020,599 | 2/1962 | Pukis et al. | 19/147 |
| 3,143,112 | 8/1964 | Sanford | 128/287 |
| 3,143,113 | 8/1964 | Mills | 604/378 |
| 3,171,773 | 3/1965 | Estes et al. | 161/168 |
| 3,371,667 | 3/1968 | Morse | 604/378 |
| 3,441,025 | 4/1969 | Ralph | 128/289 |
| 3,547,930 | 11/1970 | Blomqvist et al. | 128/284 |
| 3,630,201 | 8/1969 | Endres | 604/378 |
| 3,665,921 | 5/1972 | Stumpf | 604/378 |
| 3,825,006 | 6/1974 | Ralph | 604/378 |
| 3,844,288 | 10/1974 | Kiela | 128/287 |
| 4,197,849 | 4/1980 | Bostick | 604/318 |
| 4,285,342 | 8/1981 | Mesek | 128/287 |
| 4,411,660 | 10/1983 | Dawn et al. | 604/378 |

FOREIGN PATENT DOCUMENTS 2042342 9/1980 United Kingdom ............... 604/349

OTHER PUBLICATIONS

Four Volume Text, Absorbent Products Markets, Part I (Tampons, Diapers, Feminine Pads).
Two Volume Text, Absorbent Products Markets, Part II (Adult Incontinent Products).

Primary Examiner—C. Fred Rosenbaum
Assistant Examiner—Sherri E. Vinyard
Attorney, Agent, or Firm—Price, Heneveld, Huizenga & Cooper

[57] ABSTRACT

The specification discloses a disposable diaper having improved liquid receiving and retaining capabilities. The diaper includes a waterproof barrier formed as a flattened bag and having a single opening located adjacent the perineal area of the body of the wearer. Two layers of filler material are positioned within the barrier bag. The upper layer adjacent the opening is a wicking material, while the lower layer is a superabsorbent material. In a male version of the diaper, a pouch is formed over the opening into which the wearer's penis is inserted to direct voided urine through the bag opening.

21 Claims, 5 Drawing Figures

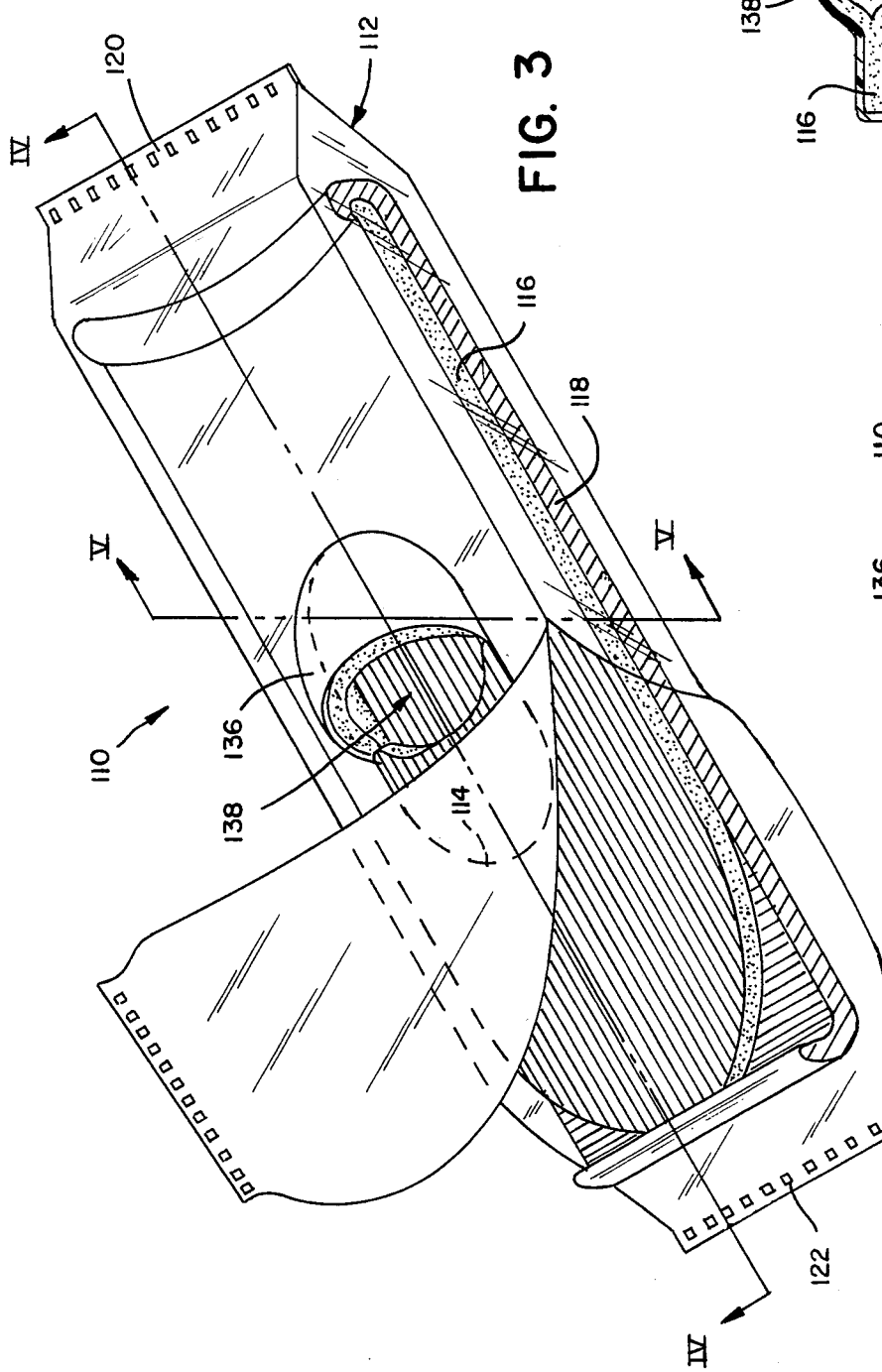
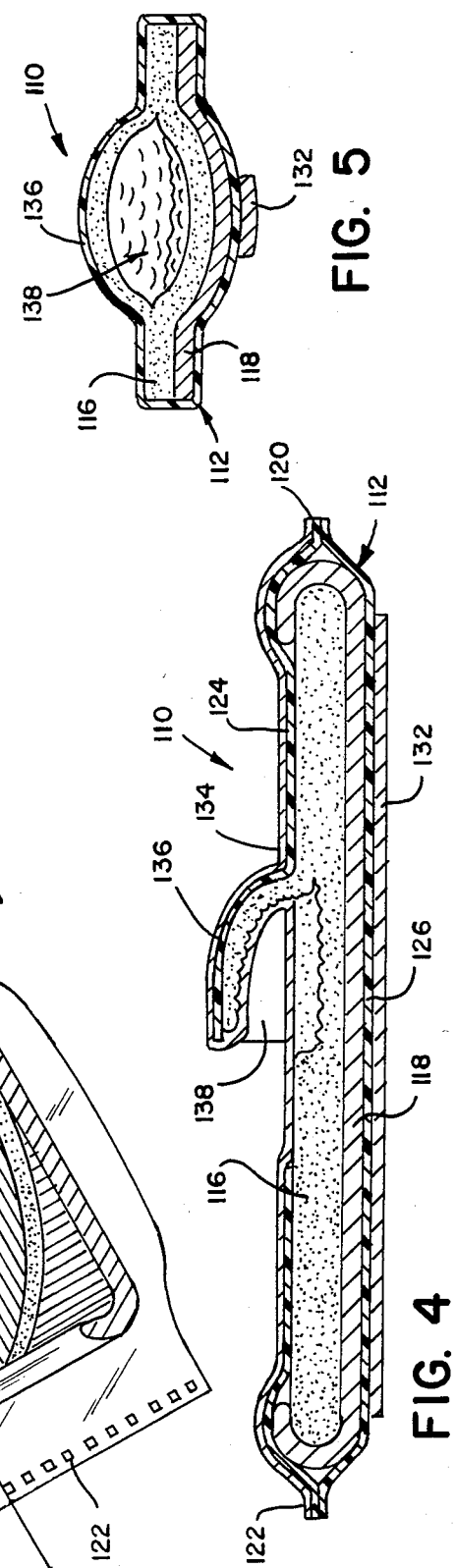

DISPOSABLE INCONTINENCE DIAPER

BACKGROUND OF THE INVENTION

The present invention relates to incontinence products, and more particularly to disposable incontinence products.

A wide variety of incontinence products have been developed for the incontinent adult. These products are typically disposable and include a water impervious barrier sheet and an absorbent material positioned thereon. In use, the waterproof barrier supports the absorbent material against the wearer's body, such that the absorbent material is positioned to absorb voided urine.

In one particularly effective product, the water impervious layer is formed as a flattened bag having a single opening proximate the perineal area of the wearer. An absorbent material is located within the bag and accessible through the opening. Examples of this type of diaper are disclosed in U.S. Pat. Nos. 4,285,342, entitled DISPOSABLE DIAPER, issued Aug. 25, 1981, to Mesek; 2,201,255, entitled DISPOSABLE DIAPER HOLDER, issued May 21, 1940, to Wilson; and 2,532,029, entitled DIAPER, issued Nov. 28, 1950, to Medoff.

However, these diapers are not without their drawbacks. Most importantly, the absorbent material within the bag is typically incapable of adequately rapidly absorbing a high flow rate of voided urine. Consequently, the voided urine will often overflow the diaper, resulting in the wetting of the wearer's clothes. Second, these diapers are best suited for women where the diaper bag opening can be located proximate the urethra to properly receive urine. These diapers are a problem for males wherein the position of the urethra outlet shifts with activity of the wearer and often is not directed into the bag opening at the time of voiding. If urine is voided when the urethra is not directed toward the opening, the urine simply flows off the water impervious bag and wets the wearer's clothes.

Although male drip absorbing devices are known, these devices typically do not include sufficient volume of absorbent to receive a full volume of voided urine. Further, known devices are awkward to use and expose the user to undesirable urine contact against large areas of the skin. Examples of known drip-absorbing products are shown in U.S. Pat. Nos. 2,873,740, entitled DISPOSABLE URINE DRIP ABSORBING DEVICE, issued Feb. 17, 1959, to Wainwright; and 2,445,220, entitled URINARY PAD, issued July 13, 1948, to Isaacson.

SUMMARY OF THE INVENTION

The aforementioned problems are overcome by the present invention. Essentially, an incontinence product is provided including a waterproof barrier formed into a flattened, substantially closed bag having a perineal opening in one side. In a first aspect of the invention, the bag is filled with two layers of material. The first material adjacent the opening is a wicking material selected for relatively rapid liquid transfer, rather than liquid absorption, characteristics. The second material is an absorbent material selected to absorb the voided liquid transported away from the bag opening. Consequently, when the wearer voids into the product, the wicking material rapidly accepts and conveys the large volume of urine away from the opening to a large portion of the absorbent material to eliminate overflow problems. Therefore, even with relatively large volumes and flow rates of voided urine, the diaper is capable of transporting and absorbing the volume sufficiently rapidly to prevent wetting of the wearer's clothes.

In a second aspect of the invention, a male incontinence product includes a similar flattened bag fabricated of water impervious material and defining a perineal opening in one side. A filler material is located within the bag for wicking and/or absorbing urine. At least one part of the bag and the filler material provides a pouch structure adjacent the bag opening to receive the wearer's penis to insure that the urethra outlet is directed into the bag opening. Consequently, when this version of the invention is worn, the pouch insures that voided urine will be directed into the bag interior to be absorbed by the material therein, reducing the possibility of urine overflow.

These and other objects, advantages, and features of the invention will be more readily understood and appreciated by reference to the detailed description of the preferred embodiments and the drawings.

BRIEF DESCRIPTION OF THE DRAWINGS

FIG. 3 is a perspective view of an alternative embodiment of the diaper with the water impervious bag partially separated to show the bag interior;

FIG. 4 is a sectional view taken along plane IV—IV in FIG. 3 and additionally showing a facing material overlying the bag; and FIG. 5 is a sectional view taken along plane V—V in FIG. 3.

DETAILED DESCRIPTION OF THE PREFERRED EMBODIMENTS

Figure 2:
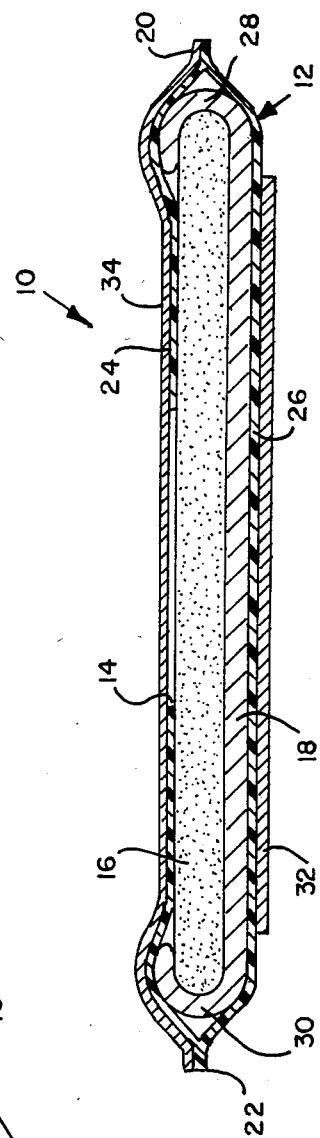
FIG. 2 is a sectional view taken along plane II—II in FIG. 1 and additionally showing a facing material overlying the bag.
Figure 1:
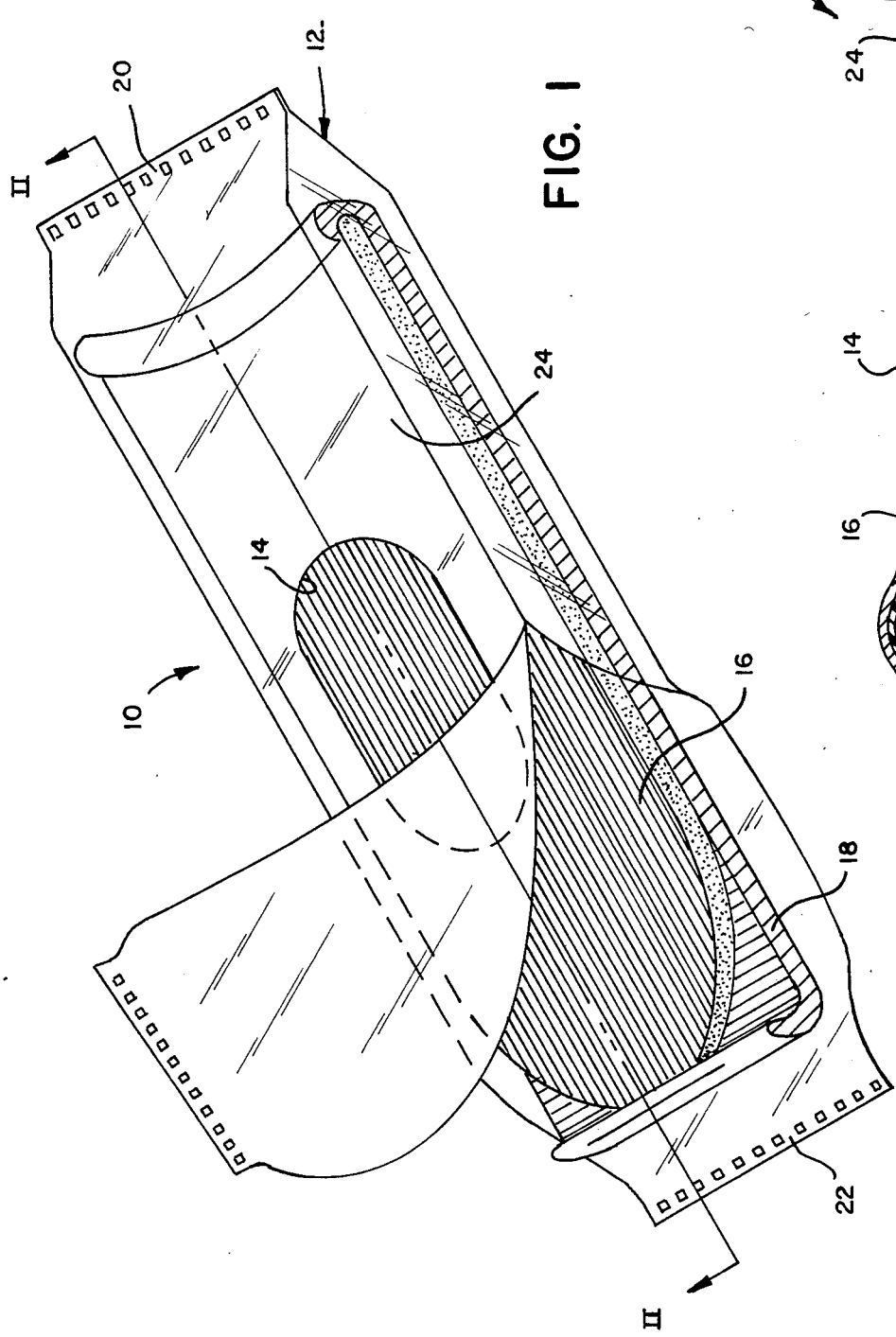
FIG. 1 is a perspective view of the incontinence diaper of the present invention with the water impervious bag partially separated to show the bag interior.

An incontinence diaper or product constructed in accordance with a preferred embodiment of the invention is illustrated in FIGS. 1 and 2 and generally designated 10. Basically, the diaper includes liquid impervious bag 12, having single perineal opening 14, and two layers 16 and 18 of material located within the bag. Layer 18 is an absorbent material and preferably a superabsorbent material to absorb and retain urine voided into diaper 10 through opening 14. Layer 16 is a wicking material positioned between opening 14 and superabsorbent 18 to rapidly transport liquid from opening 14 to a wide area over absorbent material 18 to improve the urine reception rate of the diaper.

Turning more specifically to the construction of diaper 10, bag or liquid barrier 12 is fabricated of any suitable liquid impermeable material of tubular stock. In the preferred embodiment, either polypropylene or polyethylene having a weight of approximately 12 grams per square meter is used. Of course, other suitably impervious materials can be substituted for those of the preferred embodiment. Barrier 12 has a tube-shaped configuration and is heat-sealed or adhesively bonded using conventional techniques at each of its opposite ends 20 and 22 to form a substantially watertight bag. In the preferred embodiment, barrier 12 is approximately 8 inches long, 2.5 inches wide, and 0.75 inch deep. Opening 14 is generally elongated and formed in upper side 24 of bag 12. In the preferred embodiment, opening 14 is located generally centrally, both longitudinally and transversely, on upper side 24 and is approximately 2.5 inches long and 1 inch wide.

Wicking material 16 may be any wicking material or combination of wicking materials generally available to those in the art. "Wicking material" has a meaning generally recognized in the art as a material selected for its relatively rapid liquid transportation characteristics, rather than liquid absorption characteristics. A preferred material has a high percentage of open area to provide "reservoir" space to aid in accepting high flow rates of urine. The preferred material should be resilient and not collapse when wetted. In the preferred embodiment, material 16 comprises a liquid permeable fibrous web manufactured under the trademark CORWEB by British Vita and having a density of approximately 0.03 gm/cm$^3$. Wicking material 16 is approximately 6.5 inches long by 2.5 inches wide by 0.05 inch deep.

Superabsorbent 18 is an absorbent material selected for its liquid absorption and retention capabilities. In the preferred embodiment, absorbent 18 is three layers of the superabsorbent sold by Dow under the trademark DWAL. The dimensions of layer 18 are approximately 8.0 inches long by 2.5 inches wide by 0.25 inch deep. The opposite ends 28 and 30 of layer 18 are folded about wicking material 16 to improve absorption of liquid from the wicking material. Although layers 16 And 18 have been described as two separate materials, it will be appreciated by those having ordinary skill in the art that layers 16 and 18 could be integrated into a single material having layers with the described characteristics, and that layers 16 and 18 could themselves be composed of layers.

Adhesive strip 32 (FIG. 2) is secured to underside 26 of bag 12 in any manner well known to those having ordinary skill in the art to provide a means of adhesively securing diaper 10 to an item of wearing apparel. Preferably, facing material or layer 34 (FIG. 2) overlies the entire upper surface and sides 24 of bag 12 to improve the comfort of diaper 10. Suitable adhesive strips and facing materials are generally well known to those having ordinary skill in the art and in the preferred embodiment the facing is a thermally bonded polypropylene manufactured by Scott.

In use, adhesive strip 32 adhesively secures diaper 10 to the wearer's clothing. Preferably, opening 14 is positioned proximate the perineal area and more specifically aligned with the urethra outlet. When the wearer voids, the urine passes through opening 14 to wicking material 16, which rapidly distributes the urine over a large portion of absorbent material 18. When the urine is so distributed, absorbent material 18 is capable of absorbing a relatively large flow rate through opening 14. This reduces or even prevents overflow possibilities.

Alternative Embodiment

An alternative embodiment 110 of the diaper is illustrated in FIGS. 3-5 and intended for use by males. As in the previously described embodiment, diaper 110 generally comprises barrier bag 112, defining opening 114, and wicking and absorbing layers 116 and 118, respectively, located within the bag. Bag 112 is of tubular stock heat or adhesively sealed at opposite ends 120 and 122 and includes pouch of flap 136 extending over approximately half of opening 114. In the preferred embodiment, flap 136 is integral with bag 112; however, the flap may comprise a separate piece secured to the bag. Wicking layer 116 is split along the plane of the layer in the area directly under pouch 136 to define a pocket 138 under pouch 136. Therefore, wicking material 116 envelopes pocket 138, as illustrated in FIG. 5. Preferably, suitable facing material 134 overlies upper surface and sides 124 of bag 112 and extends into and lines pocket 138 to improve the comfort of the diaper. Adhesive strip 132 is secured to underside 126 so that the diaper may be adhesively secured to an article of clothing. The materials and dimensions of diaper 110 are substantially identical to those of diaper 10.

In use, the wearer's penis is positioned in pocket 138 to insure that any urine discharged therefrom is directed through opening 114 and into wicking layer 116 to be distributed over superabsorbent 118. Thus, diaper 110 provides even further improved liquid reception and absorption capabilities over unisex diaper 10.

The above descriptions are those of preferred embodiments of the invention. Various changes and alterations may be made without departing from the spirit and broaded aspects of the invention as set forth in the appended claims, which are to be interpreted in accordance with the principles of patent law, including the doctrine of equivalents.

The embodiments of the invention in which an exclusive property or priviledge is claimed are defined as follows:

1. An incontinence product for males comprising:
   a flattened bag fabricated of a liquid impervious material, said bag including upper and lower opposite surfaces, said upper surface defining an opening positioned to be located proximate the perineal area of a wearer when said product is worn, said bag including a single integral flap extending across and arching above said opening for receiving the wearer's penis in a direction generally parallel to said flattened bag to insure that voided urine is directed through said opening; and
   filler material means within said bag for receiving urine through said opening.

2. A male incontinence product as defined in claim 1 wherein a portion of said filler material means lies adjacent the underside of said flap to line said flap, said filler material portion being between said flap and the penis, to improve the comfort of said product.

3. A male incontinence product as defined in claim 2 further comprising a facing material overlying said upper surface and any portion of said filler material means exposed through said opening to further improve the comfort of said product.

4. A male incontinence product as defined in claim 3 wherein said filler material means comprises an absorbent material and a resilient wicking material positioned between said absorbent material and said opening and further wherein only said wicking material is exposed through said opening.

5. A male incontinence product as defined in claim 4 further comprising adhesive means secured to said lower surface for adhesively securing said product to an item of wearing apparel.

6. A male incontinence product as defined in claim 1 further comprising adhesive means secured to the other of said bag surfaces for adhesively securing said product to an item of wearing apparel.

7. A male incontinence product as defined in claim 1 wherein said filler material means comprises an absorbent material and a resilient wicking material positioned between said absorbent material and said opening and further wherein only said wicking material is exposed through said opening.

8. A male incontinence product as defined in claim 1 further comprising a facing material overlying said upper surface and any portion of said filler material means exposed through said opening to improve the comfort of said product.

9. A male incontinence product as defined in claim 7 wherein said wicking material is at least as thick as said absorbent material 10. An incontinence product as defined in claim 9 wherein said wicking material is at least approximately twick as thick as said absorbent material.

11. An incontinence product as defined in claim 10 wherein said absorbent material wraps about at least a portion of the edge of said wicking material from one side of said wicking material to the other side to improve absorption of liquid by said absorbent material.

12. An incontinence product as defined in claim 9 wherein said absorbent material wraps about at least a portion of the edge of said wicking material from one side of said wicking material to the other side to improve absorption of liquid by said absorbent material.

13. An incontinence product for males comprising:
a liquid-impervious flattened sack having upper and lower surfaces, said upper surface defining an opening into the sack interior, said sack being substantially closed except for said opening, said sack including a single integral flap extending across and arching above a portion of said opening to receive and position the wearer's penis in a direction generally parallel to said flattened sack, whereby the urethra is directed into said opening;
a resilient wicking material within said sack proximate said opening, said wicking material defining a reservoir to accept urine at a relatively rapid rate; and
an abosrbent material within said bag proximate said wicking material to absorb the urine, said wicking material being at least as thick as said absorbent material.

14. An incontinence product as defined in claim 13 wherein said wicking material is separated so that a portion of said wicking material lines the underside of said flap to improve comfort.

15. An incontinence product as defined in claim 14 further comprising a facing material overlying said upper surface and any portion of said wicking material exposed through said opening to further improve comfort.

16. An incontinence product as defined in claim 15 further comprising adhesive means secured to said lower surface for adhesively securing said product to wearing apparel.

17. An incontinence product as defined in claim 13 further comprising adhesive means secured to said lower surface for adhesively securing said product to wearing apparel.

18. An incontinence product as defined in claim 13 further comprising a facing material overlying said upper surface and any portion of said wicking material exposed through said opening to improve comfort.

19. An incontinence product as defined in claim 13 wherein said wicking material is at least approximately twice as thick as said absorbent material.

20. An incontinence produce as defined in claim 19 wherein said absorbent material wraps about at least a portion of the edge of said wicking material from one side of said wicking material to the other side to improve absorption of liquid by said absorbent material.

21. An incontinence product as defined in claim 13 wherein said absorbent material wraps about at least a portion of the edge of said wicking material from one side of said wicking material to the other side to improve absorption of liquid by said absorbent material.

* * * * *

UNITED STATES PATENT AND TRADEMARK OFFICE
CERTIFICATE OF CORRECTION

PATENT NO. : 4,559,051

DATED : December 17, 1985

INVENTOR(S) : James P. Hanson

It is certified that error appears in the above-identified patent and that said Letters Patent is hereby corrected as shown below:

Column 3, line 20: "0.05" should be --.50 --.

Column 3, line 29:
"And" should be --and--

Column 3, line 66:
"of" should be --or--

Column 4, line 22:
"broaded" should be --broader--

Column 4, line 27:
"priviledge" should be --privilege--

Column 5, line 11:
After "material" insert --.--

Column 5, line 14:
"twick" should be --twice--

Column 6, line 12:
Delete "further"

Column 6, line 29: "produce" should be -- product --.

Signed and Sealed this

Twenty-fifth Day of November, 1986

*Attest:*

DONALD J. QUIGG

*Attesting Officer*    Commissioner of Patents and Trademarks